US012507970B2

(12) United States Patent
Burbar et al.

(10) Patent No.: US 12,507,970 B2
(45) Date of Patent: Dec. 30, 2025

(54) UNINTERRUPTED COOLING SYSTEM FOR A DIAGNOSTIC MEDICAL IMAGING APPARATUS

(71) Applicant: Siemens Medical Solutions USA, Inc., Malvern, PA (US)

(72) Inventors: Ziad Burbar, Knoxville, TN (US); John Keller, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 196 days.

(21) Appl. No.: 18/689,226

(22) PCT Filed: Mar. 8, 2023

(86) PCT No.: PCT/US2023/063910
§ 371 (c)(1),
(2) Date: Mar. 5, 2024

(87) PCT Pub. No.: WO2024/186346
PCT Pub. Date: Sep. 12, 2024

(65) Prior Publication Data

US 2025/0241606 A1 Jul. 31, 2025

(51) Int. Cl.
*A61B 6/00* (2024.01)
*A61B 6/03* (2006.01)

(52) U.S. Cl.
CPC ............ *A61B 6/4488* (2013.01); *A61B 6/035* (2013.01); *A61B 6/037* (2013.01)

(58) Field of Classification Search
None
See application file for complete search history.

(56) References Cited

U.S. PATENT DOCUMENTS 5,610,968 A 3/1997 Deucher et al.
6,411,672 B1 * 6/2002 Sasaki .................. A61B 6/4488 250/370.15

(Continued)

FOREIGN PATENT DOCUMENTS

EP 2502004 9/2007
JP 2008164548 A 7/2008

(Continued)

OTHER PUBLICATIONS

International Search Report for Corresponding PCT Application No. PCT/US2023/063910, mailed Oct. 9, 2023.

(Continued)

*Primary Examiner* — Hoon K Song

(57) ABSTRACT

A passive, uninterrupted cooling system continues to absorb waste heat generated with a diagnostic medical imaging system during a patient scan, in the event of a power failure incident or disruption of cooling water supply within an imaging facility. The passive, uninterrupted cooling system incorporates one or more phase change materials (PCMs) that maintain the cooling system temperature at material's melting temperature, while absorbing the imaging system's waste heat. This enables clinicians to complete an in-progress imaging scan of a patient within the scanning system's operational temperature specifications. In some embodiments, the PCMs absorb transient heat spikes generated during patient scans, in order to maintain a relatively consistent cooling system operational temperature. In some embodiments, the passive, uninterrupted cooling system is used to cool PET/CT, PET, or CT imaging systems.

11 Claims, 7 Drawing Sheets

(56) References Cited

U.S. PATENT DOCUMENTS

| | | | | |
|---|---|---|---|---|
| 6,419,389 | B1 | 7/2002 | Fuchs et al. | |
| 7,859,845 | B2 | 12/2010 | Ullman et al. | |
| 10,085,490 | B2 | 10/2018 | Griffin et al. | |
| 10,488,533 | B2 | 11/2019 | Liu et al. | |
| 10,900,667 | B2 | 1/2021 | Field et al. | |
| 11,375,995 | B1 | 7/2022 | Bubar et al. | |
| 2008/0143331 | A1 | 6/2008 | Arik et al. | |
| 2014/0367577 | A1* | 12/2014 | Badawi | A61B 6/037 250/361 R |
| 2016/0174920 | A1* | 6/2016 | Lacey | A61B 6/4488 378/189 |
| 2020/0100742 | A1 | 4/2020 | Mueller et al. | |
| 2021/0219930 | A1* | 7/2021 | Tsuchiya | A61B 6/4241 |
| 2022/0071057 | A1* | 3/2022 | Konkle | A61B 6/4488 |

FOREIGN PATENT DOCUMENTS

| | | | |
|---|---|---|---|
| WO | 2021263275 | | 12/2021 |
| WO | 2022019954 | A1 | 1/2022 |

OTHER PUBLICATIONS

Karwacki, J, "Cooling System with PCM Storage for an Office Building: Experimental Investigation Aided by a Model of the Office Thermal Dynamics", Materials 2021, 14, 1356. https://doi.org/10.3390/ma14061356, Mar. 11, 2021.

NCT Advanced Cooling Technologies, "Phase Change Material Heat Sinks for Cooling/PCM Heat Exchanger & Thermal Storage/Thermal Storage Resources", https://www.1.act.com/resources/thermal-storage/, web page retrieved Nov. 9, 2022.

* cited by examiner

UNINTERRUPTED COOLING SYSTEM FOR A DIAGNOSTIC MEDICAL IMAGING APPARATUS

TECHNICAL FIELD

A cooling system for a diagnostic medical imaging apparatus. More particularly, a passive, uninterrupted cooling system that continues to absorb heat generated by the imaging apparatus in the event of a power failure or disruption of cooling water supply within the imaging facility.

BACKGROUND

Diagnostic medical imaging apparatuses include, by way of non-limiting example computed tomography (CT), two-dimensional digital radiography (DR), positron emission tomography (PET), magnetic resonance imaging (MRI), PET/CT, and PET/MRI modalities. Many of these imaging apparatuses or systems include a toroidal-shaped, rotating gantry structure, with a patient tube through which is inserted a patient table. The gantry circumscribes the patient table and includes one or more electromagnetic radiation detectors, which emit electrons in response to incident photons of electromagnetic radiation. In some modalities, the incident photons are transmitted X-rays (e.g., CT) or ionized radiation emissions at the higher end of the electromagnetic frequency range (e.g., PET), while in other modalities the incident photons are within the radio frequency range (e.g., MRI). The output electrons of the detector are processed by detector electronics to generate detector output signals, which are subsequently processed by the imaging apparatus to generate patient images. Exemplary electromagnetic radiation detectors include photomultiplier tubes (PMTs) and silicon photomultipliers (SiPMs). Detector electronic packages are often housed with the detectors within the gantry structure. In order to generate usable patient image information during a patient scan, the detectors and detector electronic packages (collectively referred to as photon detector assemblies or PDAs) are maintained within relatively narrow, maximum operational temperature and permissible temperature fluctuation bandwidth windows. Exceeding the desired temperature fluctuations and operational temperature bandwidth windows may result in inaccurate detector readings and/or excessive noise generation components in the readings, leading to a poorer quality set of patient images. Generally, operational controls of the scanning system terminate scanner operation and commence a system shutdown when PDA temperature appears likely to exceed its maximum operational temperature window specification.

During and between patient scans, gantries and other components of imaging systems generate cyclic, fluctuating heat. In order to maintain PDA detectors and detector electronics within desired temperature bandwidth windows, heat generated within the gantry structure is transferred out of the gantry to an external cooling system. Some external cooling systems are closed-loop cooling systems, wherein a liquid coolant, such as glycol or water, absorbs waste heat captured by an internal cooler in the scanner. Coolant in the closed loop is in turned cooled by a heat sink, such as a liquid/liquid heat exchanger, which transfers coolant heat to the imaging facility's water system.

When there is a disruption of the facility's water system supply to the external heat exchanger of the external cooling system, coolant temperature rises above the PDA maximum temperature window specification, causing scanning system shutdown. The scanning system has a limited run time before it starts to overheat. This run time may vary depending on the operational state of the system; however, this time is often not sufficient to complete a patient scan.

If a system water supply disruption occurs while a patient is being scanned, the scan will be aborted, and the patient will be inconvenienced to schedule a replacement scan. A patient of an aborted PET scan was already injected with a relatively costly radiotracer. Rescheduling a new PET scan requires another radiotracer injection, which costs time and money to the patient and the imaging facility. If it were possible to continue operation of the PET scanner for about another ten minutes after water supply disruption, the scan could be competed and there would be no need to reschedule the procedure.

SUMMARY

In the exemplary embodiments described herein, a passive, uninterrupted cooling system continues to absorb waste heat generated within a diagnostic medical imaging system during a patient scan, in the event of a power failure incident or disruption of cooling water supply within the associated imaging facility. The passive, uninterrupted cooling system incorporates one or more phase change materials (PCMs) that maintain the cooling system temperature at the material's melting temperature, while absorbing the imaging system's waste heat. A sufficient thermal mass of the PCM is incorporated within the cooling system to absorb imaging system waste heat for sufficient time to complete the imaging scan prior to melting of all of the material. This enables clinicians to complete an in-progress imaging scan of a patient within the scanning system's operational temperature window specifications. In some embodiments, the PCMs absorb transient heat spikes generated during patient scans, in order to maintain a relatively consistent cooling system operational temperature within the imaging system's specification window. In an exemplary embodiment, a PET/CT scanner comprises a passive, uninterrupted cooling system that incorporates one or more PCMs. In another exemplary embodiment, a PET scanner comprises a passive, uninterrupted cooling system that incorporates one or more PCMs. In other exemplary embodiments, CT and/or PET/CT scanners incorporate PCM in its X-ray source, subcooling system.

An exemplary embodiment of the disclosure features a passive, uninterrupted cooling system for a diagnostic medical imaging scanner, comprising a diagnostic medical imaging scanner selected from an imaging modality group consisting of PET or CT or combined PET/CT. The scanner has a patient table circumscribed by a gantry, and a photon detector assembly (PDA) coupled to the gantry. The PDA has a maximum operating temperature window during a patient imaging scan. An internal cooler in the scanner is in thermal communication with the gantry and the PDA. The internal cooler has a coolant intake and a coolant exhaust, for capturing internal waste heat generated within the scanner during a patient imaging scan and maintaining PDA temperature below its maximum operating temperature window. An external cooling system, outside the scanner, circulates liquid coolant in a closed-loop coolant conduit into the coolant intake and out of the coolant exhaust of the internal cooler, where the circulating coolant extracts captured internal waste heat from the internal cooler while flowing there through. The external cooling system includes a liquid/liquid, external heat exchanger in the closed-loop conduit upstream of the coolant intake of the internal cooler, for extracting and transferring heat from the circulating coolant to a water supply of a facility water system. Heat transfer rate through the external liquid/liquid heat exchanger is sufficient to maintain coolant temperature at the coolant intake of the internal cooler below the PDA maximum operating temperature window. A heat sink is oriented in the closed-loop, coolant conduit, downstream of the external heat exchanger and upstream of the coolant intake of the internal cooler. The heat sink includes therein a first phase change material (PCM) oriented external the conduit and in conductive thermal communication with the coolant. Melting temperature of the first PCM is below the PDA maximum operating temperature window and the below coolant temperature exiting the liquid/liquid external heat exchanger. When coolant temperature entering the heat sink exceeds the first PCM melting temperature, the material absorbs latent heat from the coolant and maintains coolant inlet temperature below the PDA maximum operating temperature window for a designated time duration that is sufficient to perform a complete patient scan.

In some embodiments, the uninterrupted cooling system further comprises a CT scanner, having a rotating CT gantry having coupled thereto an X-ray source retained in a sealed X-ray housing, and an oil cooler in thermal communication with the internal cooler in the scanner. The oil cooler comprises a closed-loop oil conduit that includes within the closed loop: oil inlet and outlet lines coupled to and in fluid communication with the X-ray housing, an oil pump circulating oil in the oil conduit for cooling the X-ray source, and a second phase change material (PCM) oriented external the oil conduit, in conductive thermal communication with the circulating oil. The second PCM absorbs latent heat from the circulating oil during phase change from solid to liquid, for buffering transient heat spikes generated by the X-ray source during patient imaging scans. The second PCM transfers its absorbed latent heat to the scanner's internal cooler in time intervals between the generated transient heat spikes.

In some embodiments, the uninterrupted cooling system further comprises a PET/CT scanner, each scanner portion having respective gantries including therein a PDA, with each gantry circumscribing the patient table. The CT scanner includes a second PCM in its rotating gantry, as described above. Both scanner modalities in the PET/CT scanner share a common external cooling system as described above. A PET coolant intake of the PET internal cooler is oriented in the closed-loop coolant conduit downstream of the CT coolant exhaust of the CT internal cooler. The second PCM of the CT scanner's oil cooler retains absorbed latent heat generated by the X-ray source upon disruption of water supply to the external heat exchanger of the external cooling system, thereby reducing latent heat absorbed by the first PCM in the heat sink of the external cooling system.

Another exemplary embodiment of the disclosure features a method for passive, uninterrupted cooling of a diagnostic medical imaging scanner in the event of disruption of facility cooling water supply to a water-cooled, external cooling system of the scanner. The method is performed with a diagnostic medical imaging scanner selected from an imaging modality group consisting of PET or CT or combined PET/CT. The scanner has a patient table circumscribed by a gantry, and a photonic detector assembly (PDA) coupled to the gantry. The PDA has a maximum operating temperature during a patient imaging scan. An internal cooler in the scanner is in thermal communication with the gantry and the PDA; it has a coolant intake and a coolant exhaust, for capturing internal waste heat generated within the scanner during a patient imaging scan and for maintaining PDA temperature below its maximum operating temperature window. An external cooling system is oriented outside the scanner; it circulates liquid coolant in a closed-loop coolant conduit into the coolant intake and out of the coolant exhaust of the internal cooler. The circulating coolant extracts captured internal waste heat from the internal cooler while flowing there through. More particularly, the external cooling system has a liquid/liquid, external heat exchanger in the closed-loop conduit upstream of the coolant intake of the internal cooler, for extracting and transferring heat from the circulating coolant to a water supply of a facility water system. Heat transfer rate through the external liquid/liquid heat exchanger is sufficient to maintain coolant temperature at the coolant intake of the internal cooler below the PDA maximum operating temperature window. During routine, steady-state operation of the external cooling system, the external heat exchanger transfers heat from the circulating coolant to the water supply of the facility water system. The external cooling system also has a heat sink in the closed-loop, coolant conduit, downstream of the external heat exchanger and upstream of the coolant intake of the internal cooler, to provide back-up, uninterrupted cooling to the coolant in the event of a disruption of the facility water supply to the external heat exchanger. The heat sink includes therein a first phase change material (PCM) that is oriented external the conduit and in thermal communication with the coolant. The first PCM's melting temperature is below the PDA maximum operating temperature and below the coolant temperature exiting the external heat exchanger. When initiating a patient imaging scan with the scanner, the external cooling system circulates coolant through the coolant loop and transfers heat from the circulating coolant to the water supply of the facility water system, thus maintaining PDA temperature below its maximum operating temperature. In the event of a disruption of water supply of the facility water system to the liquid/liquid external heat exchanger, raising the coolant temperature entering the heat sink above the first PCM's melting temperature, the material absorbs, as latent heat, the captured internal waste heat that was extracted from the internal cooler by the coolant, as a substitute for the external heat exchanger. The first PCM in the heat sink maintains coolant inlet temperature below the PDA maximum operating temperature for a designated time duration sufficient to complete the patient scan. As a result, the patient scan is completed during the designated time duration.

In other method embodiments, a second PCM is oriented in the gantry, thermally coupled to the internal cooler, for capturing and buffering transient spikes in internal waste heat generated within the scanner during a patient imaging scan. Buffered waste heat is transferred from the second PCM to the internal cooler at a steady state while the external heat exchanger of the external cooling system transfers heat from the circulating coolant to the water supply of the facility water system. Upon disruption of water supply to the external heat exchanger, the second PCM retains additional waste heat generated in the scanner as latent heat, until complete melting of the second PCM. This reducing temporarily the quantity of waste heat transferred to the coolant of the external cooling system that otherwise would be transferred to the first PCM in the heat sink. Thus, the two PCMs share the waste heat load carried by the coolant during disruption of the facility water supply to the external heat exchanger.

The respective features of the exemplary embodiments of the disclosure that are described herein may be applied jointly or severally in any combination or sub-combination.

BRIEF DESCRIPTION OF DRAWINGS

The exemplary embodiments of the invention are further described in the following detailed description in conjunction with the accompanying drawings, in which.

To facilitate understanding, identical reference numerals have been used, where possible, to designate identical elements that are common to the figures. The figures are not drawn to scale.

DESCRIPTION OF EMBODIMENTS

Exemplary embodiments of the invention are utilized in a passive, uninterrupted cooling system that continues to absorb waste heat generated with a diagnostic medical imaging system during a patient scan, such as in a PET, CT or PET/CT imaging system, in the event of a power failure incident or disruption of cooling water supply within an imaging facility. The passive, uninterrupted cooling system includes a "backup", passive heat sink, which incorporates one or more phase change materials (PCMs) that maintain the cooling system temperature at material's melting temperature, while absorbing the imaging system's waste heat during the material's melting transitional phase. This enables clinicians to complete an in-progress imaging scan of a patient within the scanning system's operational temperature window specifications. In some embodiments, the PCMs absorb transient heat spikes generated during patient scans, in order to maintain a relatively consistent cooling system operational temperature.

Phase change material absorbs or releases a relatively large amount of heat when it changes state or phase. Using PCM in a "standby," passive heatsink requires a mass of the material that is sufficient to absorb the heat from the PET system over a designated period of time to complete an ongoing scan after disruption of the facility water supply to the scanner's external cooling system. For this standby application, this period of time is the maximum required time for a PET scan to be completed after facility cooling water supply is interrupted. This time can be defined to be between 7-10 minutes, with the longer period chosen for margin of error. Generally, the external cooling system requirement is for the facility supply water cooling temperature to be in the range of 4-12° C. As an example, the typical heat generated by a PET scanner to complete a PET scan is 3.2 KW for 25 cm, axial Field of View (aFoV) scan, and up to 10 KW for a long aFoV PET system of 1 meter long. The PET PDA operating temperature is in the range of 23° C. Based on this input information, one can calculate the required mass/volume of PCM needed to maintain such temperature for the time required.

Figure 1:
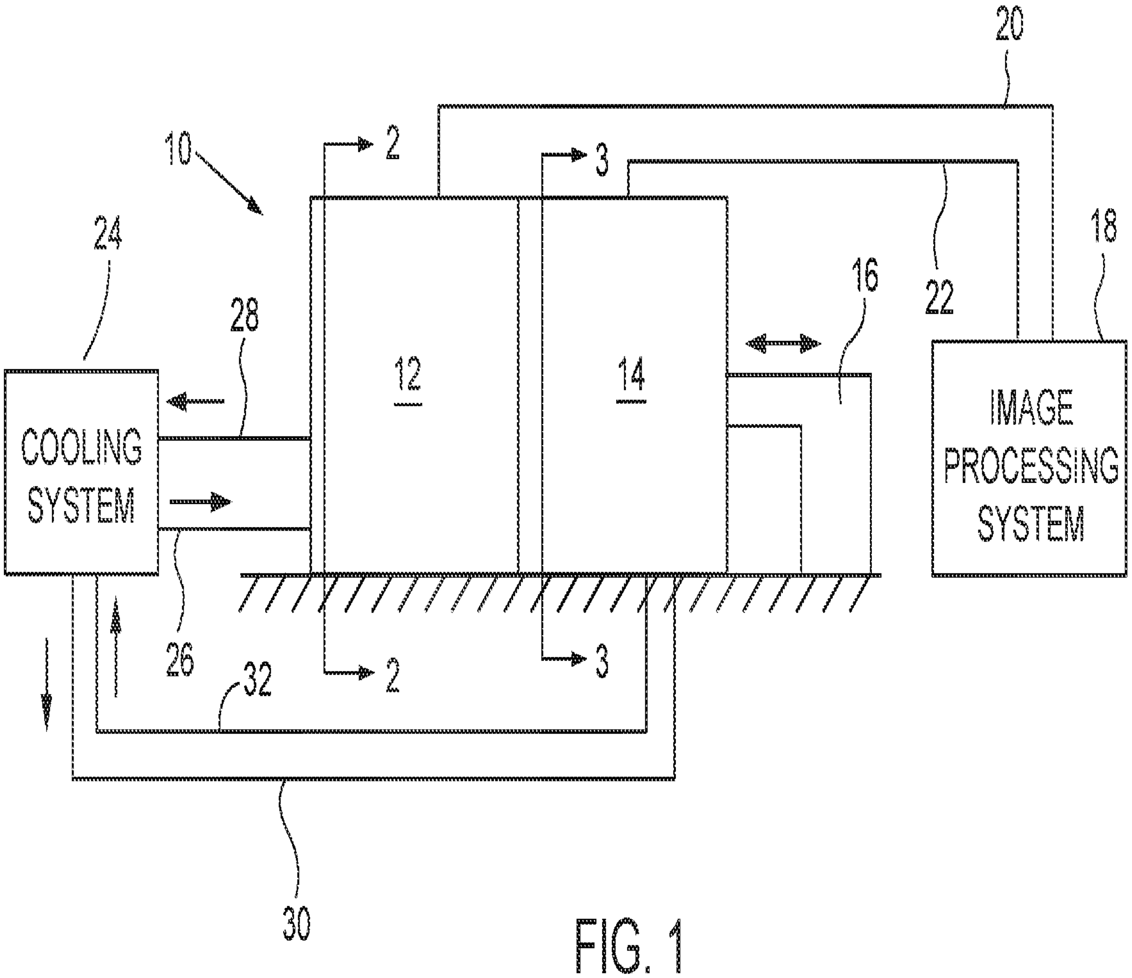
FIG. 1 is schematic, side elevational view of a combination PET/CT, diagnostic medical imaging apparatus, for generating PET and/or CT images of a patient, and its cooling system.
Figure 2:
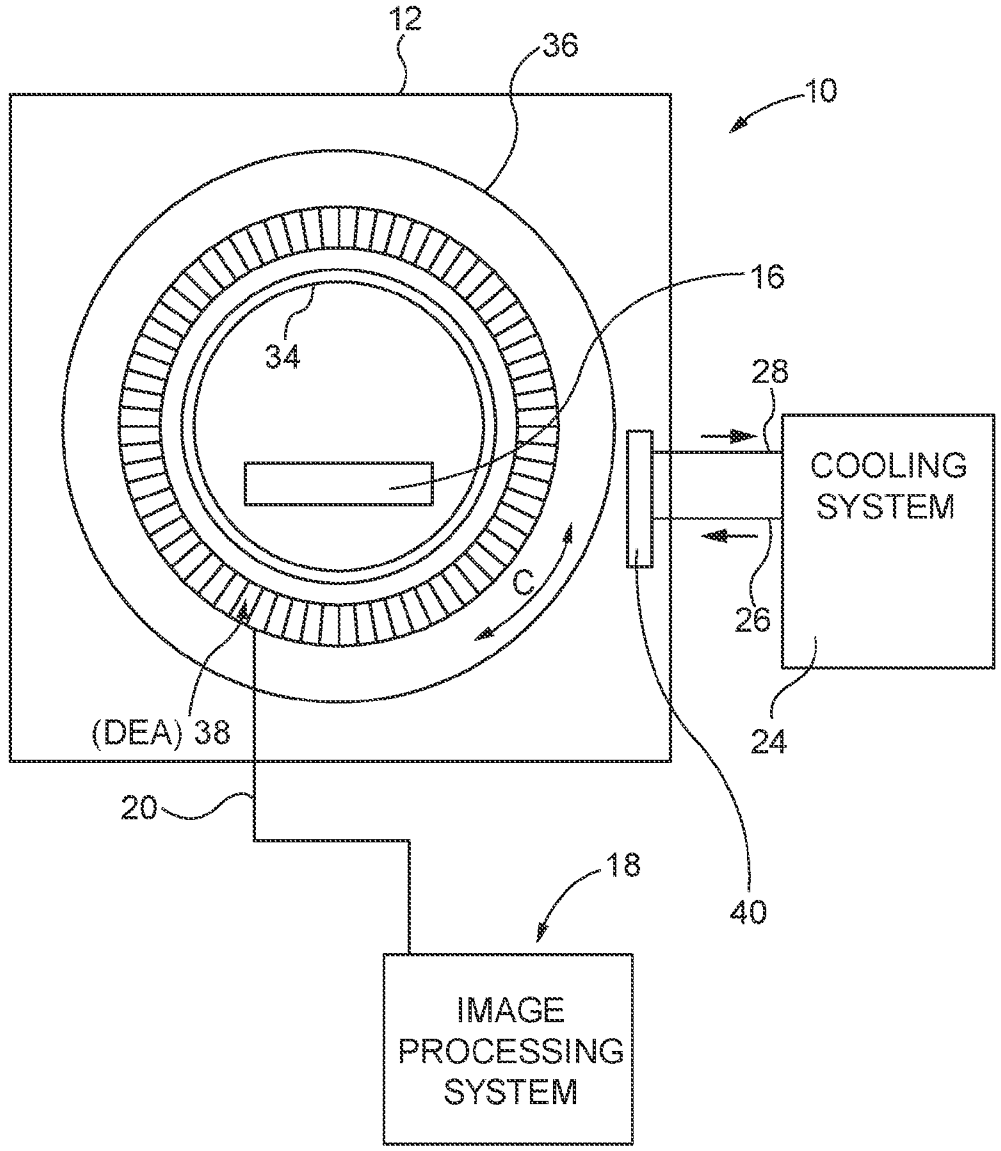
FIG. 2 is a transverse, cross-sectional view of the PET scanner portion of the imaging apparatus and cooling system of FIG. 1.
Figure 3:
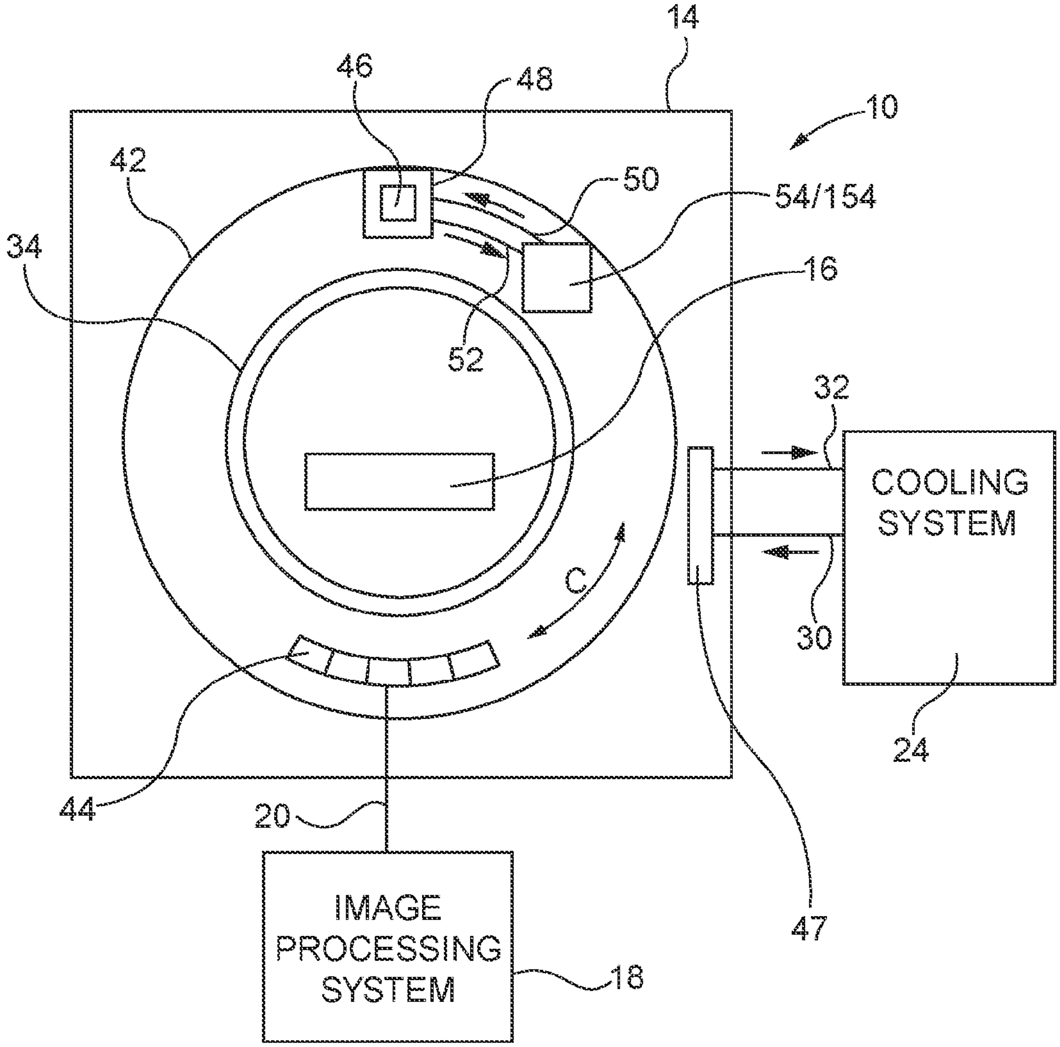
FIG. 3 is a transverse, cross-sectional view of the CT scanner portion of the imaging apparatus and cooling system of FIG. 1.
Figure 8:
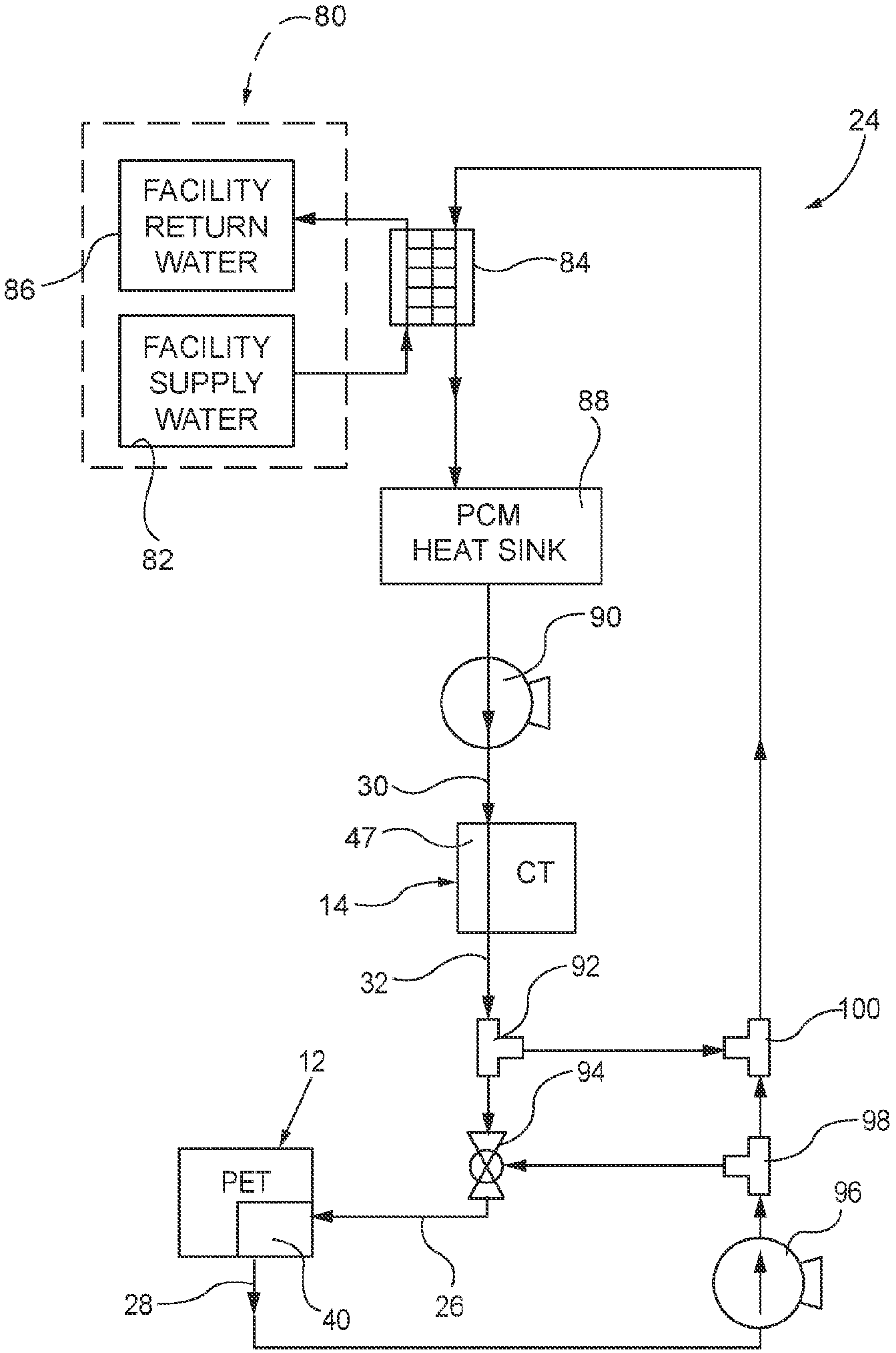
FIG. 8 is a schematic of the passive, uninterrupted cooling system of the PET/CT scanner of FIG. 1.

FIGS. 1-3 show an exemplary embodiment of a PET/CT imaging system 10, which includes a PET modality scanner 12, a tandem, coaxially aligned, CT modality scanner 14, and a translatable patient table 16. An image processing system 18 is in communication with the PET scanner 12 via communications pathway 20 and with the CT scanner 14 via communications pathway 22. Waste heat generated by PET/CT imaging system 10 is transferred to cooling system 24 by circulating coolant fluid, such as water or glycol. In these figures, the cooling system 24 is depicted as a functional block representing all components of the cooling system that are external the PET/CT imaging system 10, including all of the components and their interconnections depicted in FIG. 8. In FIG. 1, the PET coolant intake 26 receives circulating coolant from the cooling system 24, transfers waste heat generated within the PET scanner 12 to the circulating coolant and returns now warmer coolant to the cooling system through the PET coolant exhaust 28. Similarly, the CT coolant intake 30 receives circulating coolant from the cooling system 24, transfers waste heat generated within the CT scanner 14 to the circulating coolant and returns now warmer coolant to the cooling system through the CT coolant exhaust 32. In the embodiment of FIG. 8, the cooling systems of the CT 14 and PET 12 scanners are coupled serially to the external cooling system 24, so that the CT coolant exhaust 32 is upstream of the PET coolant intake 26. In other embodiments, the cooling systems of the CT 14 and PET 12 scanners are coupled in parallel to the external cooling system 24.

The transverse cross-sectional view of the PET scanner 12 of FIG. 2 shows the patient table 16 oriented within the patient tube 34 and a PET gantry 36 that circumscribes the patient tube and rotates as shown by the arrow C. In other embodiments, the PET gantry 36 does not rotate. The PET gantry 36 incorporates a detector electronics assembly (DEA) 38 as its PDA, with known detectors and related acquisition electronics. For brevity, other known components within the PET gantry 36, such as a DEA cooling subsystem and power supply, are not shown. Various embodiments of known cooling subsystems for the PET scanner 12 and its PET gantry 36 include exhaust cooling fans, fluid coolant channels and conductive heat sinks, radiators, as well as air/fluid and fluid/fluid heat exchangers that are referred to as a PET internal cooler 40 and shown as a schematic diagram block in the figures. The PET internal cooler 40 generally operates to maintain the DEA 38 within a defined ambient operating temperature bandwidth window (e.g., in some embodiments a window of 23° C.+/−2° C., but window parameter specifications are different for other embodiments of PET scanners), by transferring waste heat generated within the PET scanner 12 to the circulating coolant that it receives from the PET coolant intake 26 and discharges now warmer circulating coolant through the PET coolant exhaust 28.

The transverse cross-sectional view of the CT scanner 14 of FIG. 3 shows the patient table 16 oriented within the patient tube 34 and a CT gantry 42 that circumscribes the patient tube and rotates as shown by the arrow C. The CT gantry 42 incorporates a CT data measurement system (DMS) 44 as its PDA, with known detectors and related acquisition electronics, and an X-ray source 46 for generating the incident photons that are detected by the DMS. For brevity in FIG. 3, other known components within the CT gantry 42, such as the cooling subsystem and power supply, are not shown. Various embodiments of known cooling subsystems for the CT scanner 14 and its CT gantry 42 include exhaust cooling fans, fluid coolant channels and conductive heat sinks, radiators, as well as air/fluid and fluid/fluid heat exchangers that are referred to as a CT internal cooler 47 and shown as a schematic diagram block in the figures. The CT internal cooler 47 generally operates to maintain the CT scanner 14 within a defined ambient operating temperature bandwidth window (e.g., in some embodiments a window of 23° C.+/−2° C., but the window varies in other embodiments of CT scanners), by transferring waste heat generated within the CT scanner to the circulating coolant that it receives from the CT coolant intake 30 and discharges now warmer circulating coolant through the CT coolant exhaust 32.

Figure 4:
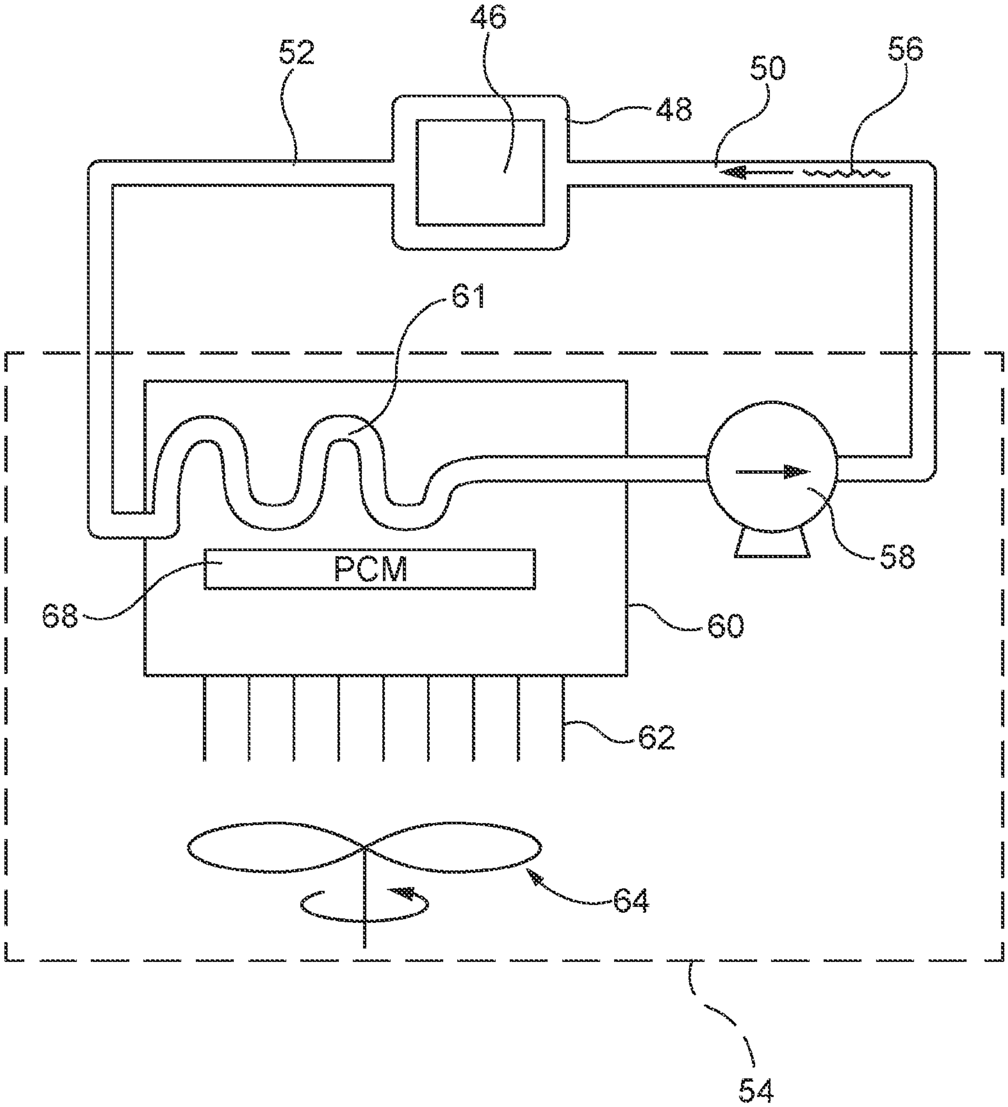
FIG. 4 is a schematic of a first embodiment of an X-ray source, cooling subsystem of the CT scanner portion of FIG. 3.

Of particular note, the X-ray source 46 in the CT scanner 14 generates relatively high-temperature waste heat, in cyclic, transient bursts during a CT scan, which is absorbed in a circulating, closed loop, oil cooling subsystem. The oil cooling subsystem includes an X-ray source housing 48 that surrounds the X-ray source 46 in a high-temperature flash-point, cooling oil. Oil inlet line 52 circulates cooling oil into the X-ray source housing 48 where it absorbs heat generated by the X-ray source 46. Heated cooling oil circulates out of the housing 48 via oil outlet line 52 where it is cooled by exemplary embodiments of oil coolers 54 or 154, shown as a schematic block 54/154. FIG. 4 shows a first embodiment, air-cooled, oil cooler 54 while FIG. 5 shows a second embodiment, liquid-cooled, oil cooler 154.

In FIG. 4, the air-cooled, oil cooler 54 circulates cooling oil 56 with a cooling pump 58 through the oil inlet 50 into the X-ray source housing 48. While in the housing 48, the circulating oil 56 absorbs heat generated by the X-ray source 46. The cooling pump 58 causes the heated circulating oil 56 to be discharged out of the oil outlet line 52 and into an oil radiator 60, where the oil is cooled for recirculation in the closed loop. The oil radiator 60 is a hybrid liquid/air heat transfer apparatus, having a plurality of cooling oil tubes 61 (only one is shown in FIG. 4) for conductive heat transfer to a plurality of cooling fins 62; the cooling fins in turn transfer heat by convection to ambient air within the CT gantry 42. Cooling fan 64 circulates ambient air over the cooling fins 62 to enhance the convective heat transfer rate. The oil radiator 60 also comprises a thermal mass of phase change material (PCM) 68 that is in conductive heat transfer communication with the circulating oil, 56 but isolated from and not in fluid communication the oil. Fluid isolation of the PCM 68 from the cooling oil 56 advantageously prevents disintegration and entrainment of the PCM within the oil, which may degrade oil quality, and potential clogging of the cooling oil tubes 61 within the oil radiator 60. Physical properties of the PCM 68 and its performance benefits for the oil cooler 54 and cooling system 24 are described below, with reference to FIGS. 6 and 7. Specifically, the PCM 68 buffers transient temperature spikes generated by the X-ray source 46 during patient scans, so that the waste heat expelled by the oil radiator 60 to the CT internal cooler 47 is more constant during the scan. In CT scanners incorporating the oil cooler 54, ambient air within the CT gantry 42 that is heated by the oil radiator 60 is in turn cooled by an air/fluid heat exchanger within the CT internal cooler 47, where waste heat is ultimately transferred to the cooling system 24 via the CT coolant exhaust 32.

Figure 5:
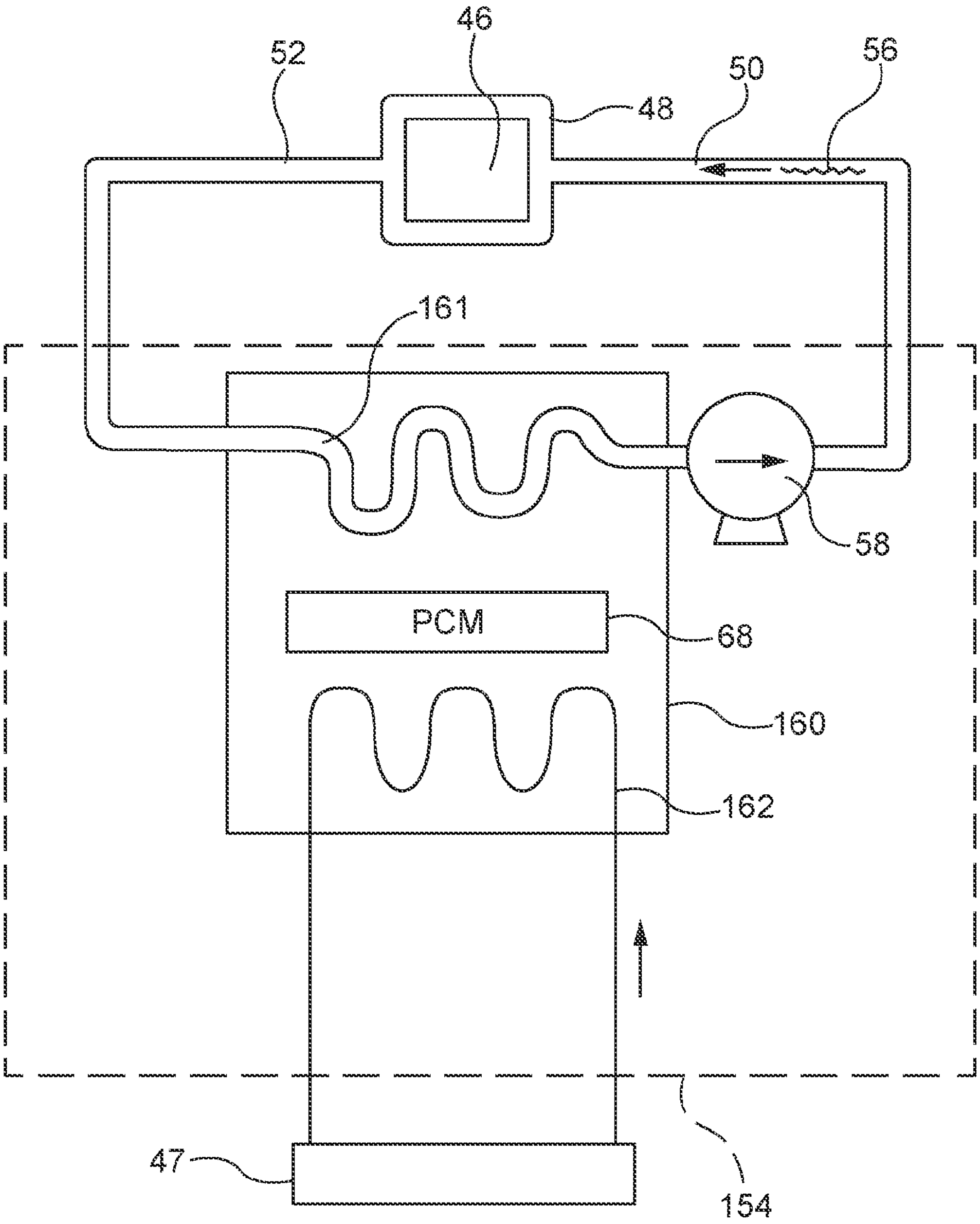
FIG. 5 is a schematic of a second embodiment of an X-ray source, cooling subsystem of the CT scanner portion of FIG. 3.

In FIG. 5, liquid-cooled, oil cooler 154 circulates cooling oil 56 with a cooling pump 58 through the oil inlet 50 into the X-ray source housing 48. While in the housing 48, the circulating oil 56 absorbs heat generated by the X-ray source 46. The cooling pump 58 causes the heated circulating oil 56 to be discharged out of the oil outlet line 52 and into an oil/liquid, coolant heat exchanger 160, where the oil is cooled for recirculation in the closed loop. The oil heat exchanger 160 is a hybrid liquid/liquid heat transfer apparatus, having a plurality of cooling oil tubes 161 for conductive heat transfer to a plurality of coolant tubes 162. For simplicity of FIG. 5, only one oil tube 161 and only one coolant tube 162 is shown. The oil heat exchanger 160 also comprises a thermal mass of phase change material (PCM) 68 that is in conductive heat transfer communication with the circulating oil 56 but isolated from and not in fluid communication the oil. Fluid isolation of the PCM 68 from the cooling oil 56 advantageously prevents disintegration and entrainment of the PCM within the oil, which may degrade oil quality, and potential clogging of the cooling oil tubes 161 within the oil heat exchanger 160. Physical properties of the PCM 68 and its performance benefits for the oil cooler 154 and cooling system 24 are described below, with reference to FIGS. 6 and 7. Specifically, the PCM 68 buffers transient temperature spikes generated by the X-ray source 46 during patient scans, so that the waste heat expelled by the oil heat exchanger 160 is more constant during the scan. In CT scanners incorporating the oil cooler 154, the coolant circulating within the coolant tubes 162 that is heated by the oil 56 is in turn cooled by the internal cooler 47, where waste heat is ultimately transferred to the cooling system 24 via the CT coolant exhaust 32. In some embodiments of the CT internal cooler 47, the coolant tubes 162 transfer heat to a second fluid/fluid heat exchanger that is intermediate the CT coolant intake 30 and CT coolant exhaust 32, for further heat transfer to the cooling system 24. In other embodiments of the CT internal cooler 47, the coolant tubes 162 are directly coupled to the CT coolant intake 30 and the CT coolant exhaust 32, for further heat transfer to the cooling system 24.

Figure 6:
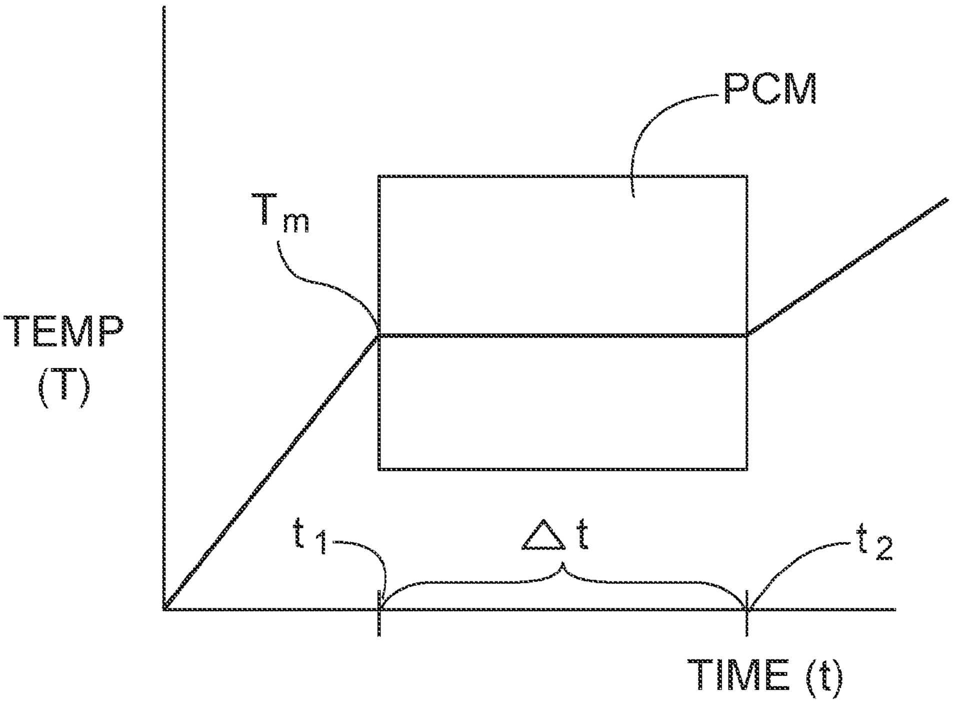
FIG. 6 is a graph of change of temperature over time of a phase change material while absorbing waste heat generated by a diagnostic medical imaging apparatus.

FIG. 6 illustrates continuous, steady-state heating of a hypothetical PCM over time. The PCM temperature rises linearly until time $t_1$ when the PCM reaches its melting temperature $T_m$ and begins latent heat absorption. The PCM maintains its melting temperature, while absorbing the applied heat, until all of the material is in liquid form at time $t_2$. Thereafter, the PCM temperature rises. The time delay, $\Delta t$ in which the PCM maintains its melting temperature, despite ongoing heat application, is a function of the applied heat in kilo Joules (kJ), the heat storage capacity of the PCM in kJ/kg and the mass quantity of material (kg). For example, various paraffin waxes have heat storage capacities of roughly 220-260 kJ/kg. Other types of exemplary phase change material compositions are selected from the group consisting of positive-temperature salt hydrates, and/or positive-temperature organics, and/or high-temperature salts.

In an exemplary embodiment, where the phase change material is RT18HC, sold by Rubitherm Technologies GmbH, Berlin, Germany, its heat storage capacity is 230 kJ/kg; and its melting temperature is $T_m$ is 18° C. As previously addressed in this disclosure, for the purpose of determining the mass quantity of PCM needed in a "standby", passive heat sink for the external cooling system, it is assumed that the facility supply water cooling temperature is in the range of 4-12° C. It is also assumed that the typical heat generated by a PET scanner to complete a PET scan is 3.2 KW for 25 cm, axial Field of View (aFoV) scan, and up to 10 KW for a long aFoV PET system of 1 meter long. The PET DEA operating temperature window specification maximum temperature is assumed to be in the range of 23° C. Assuming that the required time delay to complete a PET scan (Δt) is 10 minutes, 7.824 kg of the exemplary PCM will dissipate 3 KW of waste heat so that the temperature does not exceed 23° C. Approximately 26 kg of the same material will dissipate 10 KW of waste heat for the same time period. Other exemplary PCM materials that are potentially suitable for maintaining the exemplary PET DEA operating window temperature below 23° C. include without limitation, PureTemp 18 sold by PureTemp LLC of Minneapolis, Minnesota, USA, CrodaTherm 19 sold by Croda International Plc of East Yorkshire, United Kingdom, and PLUSICE A17 sold by PCM Products Ltd., of Cambridgeshire, United Kingdom.

Figure 7:
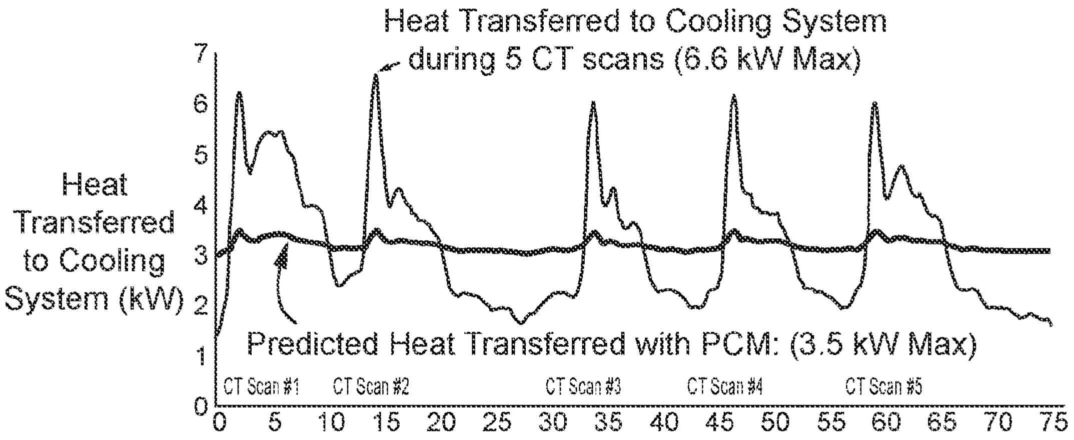
FIG. 7 a graph of cyclic waste heat generation by an exemplary CT scanner during generation of five successive CT images.

Latent heat absorption properties of the PCM 68 within the oil cooler embodiments 54 and 154 of FIGS. 4 and 5 enable those oil coolers to buffer transient, heat spikes generated by the X-ray source 46 within the CT scanner 14 of the PET/CT scanner 10. Absent the PCM 68, the oil cooler's heat transfer capacity would need to be sufficient to absorb the highest instantaneous temperature generated by the X-ray source 46 during a full scanning cycle, despite the fact that those high-temperature pulses only occur infrequently and for short time durations during a complete patient scan cycle. FIG. 7 illustrates actual heat transfer to cooling water during 5 sequential CT scans. Instantaneous heat transfer exceeded 6.6 kW after the second scan. The bold line calculates predicted, heat transferred to and buffered an exemplary PCM 68 within an oil cooler. The predicted maximum heat transfer from the PCM 68 buffer to the rest of the cooling system 24 is 3.5 kW. Thus, incorporation of the PCM 68 within the oil cooler 54 or 154 embodiments reduces the required overall cooling capacity of the cooling system 24 by over 3 kW. In some embodiments, the CT internal cooler 47 continuously transfers heat from and cools the PCM 68, enabling the phase change material to re-solidify between transient heat spikes. In other embodiments, coolant supply to the CT internal cooler 47 is restricted or stopped completely, so that the PCM 68 absorbs more of, or all heat generated by the X-ray source 46 during all or a portion of a CT imaging scan. In this other embodiment, the material in the PCM 68 regenerates back to solid form at a later designated time, when coolant flow to the CT internal cooler 47 is increased sufficiently to enable the solidification. In an exemplary embodiment, the PCM 68 has a melting range around of 70° C. In an exemplary embodiment, the PCM 68 comprises RT70HC material sold by Rubitherm Technologies GmbH, Berlin, Germany FIG. 8 is a schematic of the passive, uninterrupted cooling system 24 of the PET/CT scanner 10, comprising a fluid, continuous flow, closed coolant loop, circulating a liquid coolant such as water. In general, flowing coolant in the coolant loop absorbs heat generated by the PDA and various other components within the PET/CT scanner 10, such as the exemplary DEA 38 of the PET scanner 12, as well as the DMS 44 with their associated electronics and the X-ray source 46 of the CT scanner 14. The circulating coolant in the closed coolant loop transfers the absorbed heat from the components of the PET/CT scanner 10 to a facility heat sink.

Here, the facility heat sink is a facility water system 80, which provides a flowing, cool water supply 82 into an intake loop of a liquid-liquid heat exchanger 84 at a temperature range between 4-12° C.; thereafter, warmer return water 86 exits the heat exchanger. The previously circulated, heated coolant discharged from the PET/CT scanner 10 flows through a corresponding outlet loop of the external heat exchanger 84, transferring heat to the return water 86, typically reducing temperature of the circulating, refreshed coolant to about the same temperature of the cool water supply 82.

After exiting the outer loop of the external heat exchanger 84, the circulating coolant passes through a PCM heat sink 88 at the same approximately 4-12° C. In some embodiments of the PCM heat sink 88, the phase change material is encapsulated within a reservoir tank and is in direct conductive and convective thermal communication with the circulating coolant. In other embodiments, the PCM heat sink 88 comprises a plurality of coolant tubes and fins, similar in construction to a radiator, with PCM sandwiched between and in direct, conductive thermal communication with some or all of the fins and tubes. Under steady state operation of the coolant system 24, temperature of the circulating coolant (approximately 4-12° C.), passing through the PCM heat sink 88 is lower than the melting temperature of the phase change material contained therein. In an exemplary embodiment, the PCM melting temperature $T_m$ is 16° C. Thus, during such steady state operation, the phase change material remains passively in its solid phase at the coolant temperature, ready to absorb latent heat should the coolant temperature rise above $T_m$.

As thermal properties of exemplary phase change material were explained with reference to FIG. 6, when and if temperature of the circulating coolant reaches the 16° C. melting temperature of the material in the PCM heat sink 88, the material therein will absorb heat from the coolant and commence its phase change from solid to liquid. As a result, temperature of the circulating the coolant exiting the PCM heat sink 88 will be maintained at the material's 16° C. melting temperature so long as sold material remains in the heatsink.

The heat absorbing material in the PCM heat sink 88 comprises a thermal mass sufficient to absorb all waste heat generated by the PET/CT scanner 10 during a specified operational time window that is necessary for maintaining scanner components within their operational temperature window specifications (e.g., maintaining the DEA 38 of the PET scanner 12 at a maximum temperature of approximately 23° C.). In an exemplary embodiment of the cooling system 24, a mass of 26 kg of Rubitherm GmbH, RTHC18 phase change material in the PCM heat sink 88 is capable of dissipating 10 KW of waste heat generated by the PET/CT scanner 10 for 10 minutes: the approximate time needed to complete a patient diagnostic imaging scan. By way of nonlimiting example of one required cooling parameter for the PET/CT scanner 10, thermal mass within the PCM heat sink 88 is sufficient to maintain the DEA 38 of the PET scanner 12 within a temperature window not to exceed 23° C. during the full imaging cycle. Generally, the thermal absorption capacity of the PCM heat sink 88 corresponds to or exceeds the equivalent thermal absorption capacity of the heat exchanger 84, so that the former can function as a passive substitute or "stand by" heat sink for the cooling system 24, in the event of a disruption of the facility water supply 82.

A first circulating pump 90 routes cooled coolant from the PCM heat sink 88 to the coolant intake 30 of the CT Scanner 14, through the CT internal cooler 47. The now hotter coolant exits the CT coolant exhaust 32 and thereafter its flow is split at a first bypass tee 92, where some or all of that fluid is routed back to the heat exchanger 84 through a second bypass tee 100. Thus, the heat exchanger 84, the PCM heat sink 88, the CT internal cooler 47 and the first and second bypass tees 92, 100 form a first coolant loop. A second coolant loop is formed downstream of the first bypass tee 92, through the mixing valve 94, into the PET coolant intake 26, the PET internal cooler 40, out the PET coolant exhaust 28, the second circulating pump 96, and a third bypass tee 98. Coolant flow discharged from the second circulating pump 96 is split at the bypass tee 98, where a portion of the flow is directed back to the mixing valve 94. The remainder of coolant flow discharged from the third bypass tee 98 is directed to the second bypass tee 100 for return in the first cooling loop back to the heat exchanger 84 for refresh cooling and repeating the flow cycle through the first and second cooling loops. In an exemplary embodiment, the refreshed coolant temperature exiting the heat exchanger 84 is approximately 4-12° C. The mixing valve 94 and the first 90 and second 96 circulating pumps 114 adjust flow rate and mixing proportions of the recirculating coolant to achieve desired heat absorption from components within the PET/CT scanner 10. The mixing valve 94 is controlled by a control program executed within the image processing system 18 or another controller of the scanner 12 that relies on temperature sensors placed at the inlets (from the tees 92 and 98 and the outlet (to the PET coolant intake 26) of the mixing valve.

The mixing valve 94 and the first circulating pump 90 circulate the coolant in the first cooling loop between the CT scanner 14 and the cooling system 24 at a first flow rate that maintains a specified stable temperature bandwidth for components within the CT scanner, including the X-ray source 46. In the exemplary embodiment, coolant flow rate in the first cooling loop and heat transfer capacity of the heat exchanger 84 are calculated to maintain coolant temperature exiting the CT coolant exhaust 32 greater than the 4-12° C. inlet temperature but below 23° C.

Cooling temperature stability within the CT scanner 14 is enhanced by embodiments of oil coolers 54 and 154, within the CT gantry 42, which incorporate PCM 68 within an oil radiator 60 or a fluid/fluid oil cooler 160. As described in the exemplary FIG. 7, the PCM in the oil cooler embodiments 54 or 154 absorb transient waste heat spikes generated by the X-ray source 46, which buffers and normalizes average temperature within the CT gantry 42 and ultimately distributes heat absorption responsibilities between the oil cooler and the overall cooling system 24. In some embodiments, the PCM 68 in the oil cooler absorbs more or all of the waste heat generated by the X-ray source 46 during a CT scan, for later release to the CT internal cooler 47, reducing overall thermal load on the external cooling system 24. In contrast, oil coolers without PCM require a CT internal cooler 47 with a higher heat absorption capacity to accommodate the transient temperature spikes generated by the X-ray source 46. The higher required heat absorption capacity increases the overall thermal load on the external cooling system 24, to assure that the coolant temperature exiting the CT coolant exhaust 32 is below the exemplary embodiment's 23° C. temperature limit for the DEA 38 in the PET scanner 12. Increasing thermal load on the external cooling system requires more external heat exchanger 84 capacity and more standby PCM heat sink 88 capacity.

Turning now to the second cooling loop in the cooling system 24, the mixing valve 94 selectively mixes proportionally coolant at a first temperature that has passed through the CT internal cooler 47 in the first coolant loop, and relatively hotter downstream coolant that has passed through the PET internal cooler 40, from the third bypass tee 98, at a flow rate established by the second cooling pump 96, to achieve a desired intake coolant temperature at the PET coolant intake 26. Coolant of the desired coolant temperature passes through the PET internal cooler 40, where it absorbs heat from the DEA 38 and any other heat generating components within the PET scanner 12. One specific coolant temperature control parameter of interest is maintaining a stable temperature bandwidth window of the detector elements in the DEA 38 within specification parameters, to avoid detector distortion. In some imaging system embodiments, where its DEA 38 incorporates SiPM detector elements, the coolant temperature bandwidth window is 23° C. within +/−2° C. for all detector elements in the PET gantry 36.

Generally, kilowatts of heat transfer capacity in the cooling system 24 is calculated to maintain specified operational temperature parameters within the PET/CT scanner 10. Waste heat absorbed by the cooling system 24 ultimately is transferred to the facility water system 80 by the external heat exchanger 84. In the event of an electrical power failure at the imaging facility, a backup uninterrupted power supply typically powers the PET/CT scanner 10, the associated first 90 and second 96 circulating pumps, and any other powered components of the cooling system 24 (e.g., control systems). It is possible to complete patient scans that were already underway prior to the power failure. In the event that the power failure disrupts ability of the facility water system 80 to supply running cooling water to the external heat exchanger 84, the PCM heat sink 88 is a passive substitute heat sink for the heat exchanger. As temperature of the circulating cooling in the first and second loops of the cooling system 24 rises to the 16° C. melting temperature of the exemplary phase change material in the PCM heat sink 88, the material in the PCM heat sink 88 starts to melt and absorb latent heat until all of that material melts. Thermal mass of the exemplary PCM in the PCM heat sink 88 is calculated to absorb the kilowatts of heat generated by the CT/PET scanner 12 for the designated time necessary to complete a scanning image: approximately ten minutes. The scanner 10 will continue to operate until all of the PCM has melted or upon scan completion. During controlled shut down of the CT/PET scanner 12 the PCM-enhanced oil cooler 54 and 154 embodiments of FIGS. 4 and 5 absorb waste some or all of the waste heat generated by the X-ray source 46, relieving thermal load that would otherwise need to be absorbed by the PCM heat sink 88. In some embodiments, after disruption of the facility water supply 80, water flow to the external heat exchanger 84, coolant supply to the CT internal cooler 47 is restricted or shut off temporarily, so that the PCM 68 in the oil cooler shares thermal load with the PCM heat sink 88. This reduces overall thermal load on the external cooling system 24 during the completion of an ongoing imaging scan.

When water circulation by the facility water system 80 is restored, in the exemplary embodiment of the cooling system 24, the external heat exchanger 84 cools the circulating coolant below the 16° C. melting temperature of the material within the PCM heat sink 88. This re-solidifies the material in the PCM heat sink 88, readying it for future passive, uninterrupted cooling of the cooling system 24 in the event of any future facility water system 88 or electrical power disruptions. Similarly, in embodiments where the PCM 68 in the CT scanner 14 has temporarily absorbed thermal load, its material regenerates and resolidifies upon circulation of coolant within the CT internal cooler 47.

While embodiments of a passive, uninterrupted cooling system have been described in this disclosure, as incorporated within a combination PET/CT modality scanner 10, other embodiments of the cooling system are incorporated in single modality PET scanners and CT scanners.

Although various embodiments have been shown and described in detail herein, others can readily devise many other varied embodiments that still incorporate the claimed invention. The invention is not limited in its application to the exemplary embodiment details of construction and the arrangement of components set forth in the description or illustrated in the drawings. The invention is capable of other embodiments and of being practiced or of being carried out in various ways. In addition, it is to be understood that the phraseology and terminology used herein is for the purpose of description and should not be regarded as limiting. The use of “including”, “comprising”, or “having”, and variations thereof herein is meant to encompass the items listed thereafter and equivalents thereof as well as additional items. Unless specified or limited otherwise, the terms “mounted”, “connected”, “supported”, and “coupled” and variations thereof are to be interpreted broadly; they encompass direct and indirect mountings, connections, supports, and couplings.

What is claimed is:

1. A passive, uninterrupted cooling system for a diagnostic medical imaging scanner, comprising:

a diagnostic medical imaging scanner selected from an imaging modality group consisting of PET or CT or combined PET/CT, the scanner having a patient table circumscribed by a gantry, a photon detector assembly (PDA) coupled to the gantry, the PDA having a maximum operating temperature, within an operating temperature window, during a patient imaging scan;

an internal cooler in the scanner, in thermal communication with the gantry and the PDA, having a coolant intake and a coolant exhaust, for capturing internal waste heat generated within the scanner during a patient imaging scan and maintaining PDA temperature below its maximum operating temperature; and an external cooling system outside the scanner, circulating liquid coolant in a closed-loop coolant conduit into the coolant intake and out of the coolant exhaust of the internal cooler, the circulating coolant extracting captured internal waste heat from the internal cooler while flowing there through, the external cooling system having:

a liquid/liquid, external heat exchanger in the closed-loop conduit upstream of the coolant intake of the internal cooler, for extracting and transferring heat from the circulating coolant to a water supply of a facility water system, with heat transfer rate through the external liquid/liquid heat exchanger sufficient to maintain coolant temperature at the coolant intake of the internal cooler below the PDA maximum operating temperature; and a heat sink in the closed-loop, coolant conduit, downstream of the external heat exchanger and upstream of the coolant intake of the internal cooler, the heat sink including therein a first phase change material (PCM) oriented external the conduit and in conductive thermal communication with the coolant, the first PCM melting temperature below the PDA maximum operating temperature; upon coolant temperature exceeding the first PCM melting temperature, the material absorbing latent heat from the coolant and maintaining coolant inlet temperature below the PDA maximum operating temperature for a designated time duration sufficient to perform a complete patient scan.

2. The uninterrupted cooling system of claim 1, the internal cooler comprising an air/fluid heat exchanger that captures internal waste heat from ambient air within the scanner, for extraction by the coolant circulating through the coolant intake and out of the coolant exhaust.

3. The uninterrupted cooling system of claim 1, the internal cooler comprising a fluid/fluid heat exchanger that captures internal waste heat generated within the scanner, for extraction by the coolant circulating through the coolant intake and out of the coolant exhaust.

4. The uninterrupted cooling system of claim 1, the first PCM selected from the group consisting of paraffin wax, and/or positive-temperature salt hydrates, and/or positive-temperature organics, and/or high-temperature salts.

5. The uninterrupted cooling system of claim 1, further comprising a CT scanner, having:

a rotating CT gantry having coupled thereto an X-ray source retained in a sealed X-ray housing, and an oil cooler in thermal communication with the internal cooler in the scanner;

the oil cooler including a closed-loop oil conduit that includes within the closed loop: oil inlet and outlet lines coupled to and in fluid communication with the X-ray housing, an oil pump circulating oil in the oil conduit for cooling the X-ray source, and second phase change material (PCM) oriented external the oil conduit, in conductive thermal communication with the circulating oil, the second PCM absorbing latent heat from the circulating oil during phase change from solid to liquid, for buffering transient heat spikes generated by the X-ray source during patient imaging scans, and the second PCM transferring its absorbed latent heat to the scanner’s internal cooler in time intervals between the generated transient heat spikes.

6. The uninterrupted cooling system of claim 5, the oil cooler further comprising an oil radiator coupled to the oil conduit, the oil radiator in thermal communication with an air/liquid internal cooler in the scanner, said internal cooler in turn coupled to the coolant intake and coolant exhaust.

7. The uninterrupted cooling system of claim 5, the oil cooler further comprising an oil/fluid heat exchanger coupled to the oil conduit, the oil/fluid heat exchanger in fluid and thermal communication with a liquid/liquid internal cooler in the scanner, said internal cooler in turn coupled to the coolant intake and coolant exhaust.

8. The uninterrupted cooling system of claim 5, the second PCM having a melting range of 70° C.

9. The uninterrupted cooling system of claim 5, further comprising:

a PET/CT scanner, respective gantries having therein a PDA, with each gantry circumscribing the patient table;

a PET coolant intake of the PET internal cooler oriented in the closed-loop coolant conduit downstream of the CT coolant exhaust of the CT internal cooler; and the second PCM of the CT scanner’s oil cooler retaining absorbed latent heat generated by the X-ray source upon disruption of water supply to the external heat exchanger of the external cooling system, thereby reducing latent heat absorbed by the first PCM in the heat sink of the external cooling system.

10. A method for passive, uninterrupted cooling of a diagnostic medical imaging scanner in the event of disruption of facility cooling water supply to a water-cooled, external cooling system of the scanner, comprising:

providing a diagnostic medical imaging scanner selected from an imaging modality group consisting of PET or CT or combined PET/CT, the scanner having: a patient table circumscribed by a gantry, a photon detector assembly (PDA) coupled to the gantry, the PDA having a maximum operating temperature, within an operating temperature window, during a patient imaging scan, an internal cooler in the scanner, in thermal communication with the gantry and the PDA, the internal cooler having a coolant intake and a coolant exhaust, for capturing internal waste heat generated within the scanner during a patient imaging scan and for maintaining PDA temperature below its maximum operating temperature;

providing an external cooling system outside the scanner, circulating liquid coolant in a closed-loop coolant conduit into the coolant intake and out of the coolant exhaust of the internal cooler, the circulating coolant extracting captured internal waste heat from the internal cooler while flowing there through, the external cooling system having: a liquid/liquid, external heat exchanger in the closed-loop conduit upstream of the coolant intake of the internal cooler, for extracting and transferring heat from the circulating coolant to a water supply of a facility water system, with heat transfer rate through the external liquid/liquid heat exchanger sufficient to maintain coolant temperature at the coolant intake of the internal cooler below the PDA maximum operating temperature, and transferring heat from the circulating coolant to the water supply of the facility water system; and providing a heat sink in the closed-loop, coolant conduit, downstream of the external heat exchanger and upstream of the coolant intake of the internal cooler, the heat sink including therein a first phase change material (PCM) oriented external the conduit and in thermal communication with the coolant, the first PCM melting temperature below the PDA maximum operating temperature;

initiating a patient imaging scan with the scanner while operating the external cooling system, by circulating coolant through the coolant loop and transferring heat from the circulating coolant to the water supply of the facility water system, maintaining PDA temperature below its maximum operating temperature;

upon disruption of water supply of the facility water system to the liquid/liquid external heat exchanger, absorbing in the heat sink's first PCM as latent heat the captured internal waste heat that was extracted from the internal cooler by the coolant, by melting the first PCM and maintaining coolant inlet temperature below the PDA maximum operating temperature for a designated time duration sufficient to perform a complete patient scan; and completing the patient scan during the designated time duration.

11. The method of claim 10, further comprising:

orienting a second PCM in the gantry, thermally coupled to the internal cooler, for capturing and buffering transient spikes in internal waste heat generated within the scanner during a patient imaging scan;

transferring buffered waste heat from the second PCM to the internal cooler at a steady state while the external heat exchanger of the external cooling system transfers heat from the circulating coolant to the water supply of the facility water system; and upon disruption of water supply to the external heat exchanger, retaining additional waste in the second PCM as latent heat, until complete melting of the second PCM, thereby reducing temporarily quantity of waste heat transferred to the coolant of the external cooling system that otherwise would be transferred to the first PCM in the heat sink.

* * * * *